(12) United States Patent
Sanagustin Aquilue et al.

(10) Patent No.: US 10,857,160 B2
(45) Date of Patent: Dec. 8, 2020

(54) OIL-IN-WATER NANOEMULSION COMPOSITION OF CLOBETASOL

(71) Applicant: LABORATORIOS SALVAT, S.A., Esplugues de Llobregat (ES)

(72) Inventors: Javier Sanagustin Aquilue, Esplugues de Llobregat (ES); María Del Carmen Lendínez Gris, Esplugues de Llobregat (ES); Maria Isabel Delgado Gañán, Esplugues de Llobregat (ES)

(73) Assignee: LABORATORIOS SALVAT, S.A., Esplugues de Llobregat (ES)

( * ) Notice: Subject to any disclaimer, the term of this patent is extended or adjusted under 35 U.S.C. 154(b) by 317 days.

(21) Appl. No.: 16/069,473

(22) PCT Filed: Jan. 18, 2018

(86) PCT No.: PCT/EP2018/051218
§ 371 (c)(1),
(2) Date: Jul. 11, 2018

(87) PCT Pub. No.: WO2018/233878
PCT Pub. Date: Dec. 27, 2018

(65) Prior Publication Data
US 2019/0298737 A1 Oct. 3, 2019

(30) Foreign Application Priority Data
Jun. 23, 2017 (EP) ..................... 17382393

(51) Int. Cl.
| A61K 31/56 | (2006.01) |
| A61K 31/573 | (2006.01) |
| A61P 29/00 | (2006.01) |
| A61K 9/00 | (2006.01) |
| A61K 9/107 | (2006.01) |
| A61K 47/02 | (2006.01) |
| A61K 47/10 | (2017.01) |
| A61K 47/26 | (2006.01) |
| A61K 47/44 | (2017.01) |
| A61K 47/14 | (2017.01) |
| A61K 47/34 | (2017.01) |

(52) U.S. Cl.
CPC ............ *A61K 31/573* (2013.01); *A61K 9/006* (2013.01); *A61K 9/0043* (2013.01); *A61K 9/0046* (2013.01); *A61K 9/0048* (2013.01); *A61K 9/1075* (2013.01); *A61K 47/02* (2013.01); *A61K 47/10* (2013.01); *A61K 47/14* (2013.01); *A61K 47/26* (2013.01); *A61K 47/34* (2013.01); *A61K 47/44* (2013.01); *A61P 29/00* (2018.01)

(58) Field of Classification Search
CPC ...................................................... A61K 31/56
USPC ........................................................ 514/178
See application file for complete search history.

(56) References Cited

FOREIGN PATENT DOCUMENTS

| EP | 0844001 A1 | 5/1998 |
| WO | WO 2017/037663 A1 | 3/2017 |

OTHER PUBLICATIONS

International Search Report and Written Opinion dated May 24, 2018 for PCT Application No. PCT/EP2018/051218, 14 pages.
(Continued)

*Primary Examiner* — Raymond J Henley, III
(74) *Attorney, Agent, or Firm* — Squire Patton Boggs (US) LLP

(57) ABSTRACT

It relates to an oil-in-water nanoemulsion composition having a continuous aqueous phase and dispersed oil droplets, wherein the nanoemulsion comprises: (a) clobetasol; (b) one or more oil components; and (c) one or more surfactants; together with one or more pharmaceutically acceptable excipients or carriers wherein: the osmolality of the nanoemulsion is comprised from 100 mOsm/Kg to 500 mOsm/Kg; the droplet average size measured by Dynamic light scattering is comprised from 1 nm to 500 nm; the weight ratio between the oil components and the sum of the oil components and one or more surfactants is comprised from 0.001 to 0.5; the weight ratio between the oil component and clobetasol is comprised from 1:1 to 200:1; and the weight ratio between the surfactant and clobetasol is comprised from 2:1 to 200:1. It also relates to processes for its preparation, its use as a medicament, and in the prophylaxis and/or treatment of inflammatory diseases or conditions.

14 Claims, 1 Drawing Sheet

(56) References Cited

OTHER PUBLICATIONS

Ali, Mohammad Sajid, et al., "Accelerated Stability Testing of a Clobetasol Propionate-Loaded Nanoemulsion as per ICH Guidelines", Apr. 2013, Scientia Pharmaceutica 2013, vol. 81, No. 4, pp. 1089-1100.
Hassan, Puthusserickal A., et al., "Making sense of Brownian Motion: Colloid characterization by dynamic light scattering", Jul. 2014, Langmuir 2015, vol. 31, pp. 3-12.
ICCVAM—Recommended Test Method Protocol: Hen's Egg Test—Chorioallantoic Membrane (HET-CAM) Test Method, NIH Publication No. 10-7553, 2010, https://ntp.niehs.nih.gov/iccvam/docs/protocols/ivocular-hetcam.pdf.
ICH Harmonised Tripartite Guidline: Impurities in New Drug Products Q3B(R2), Jun. 2, 2006, 16 pages.
Kalinec, Gilda M., et al., "A Cochlear Cell Line as an in vitro System for Drug Ototoxicity Screening", Audiology Neuro-Otology 2003, vol. 8, pp. 177-189.
OECD/OCDE, OECD Guideline for the Testing of Chemicals, Acute Eye Irritation/Corrosion 2012, pp. 1-21.
OECD/OCDE, OECD Guideline for the Testing of Chemicals, Short Time Exposure In Vitro Test Method for Identifying i) Chemicals Inducing Serious Eye Damage and ii) Chemicals Not Requiring Classification for Eye Irritation or Serious Eye Damage, 2017, pp. 1-13.
U.S. Pharmacopeia, USP Monographs: Clobetasol Propionate, downloaded Jun. 2017, http://www.pharmacopeia.cn/v29240/usp29nf24s)_m18334.html#, 2 pages.

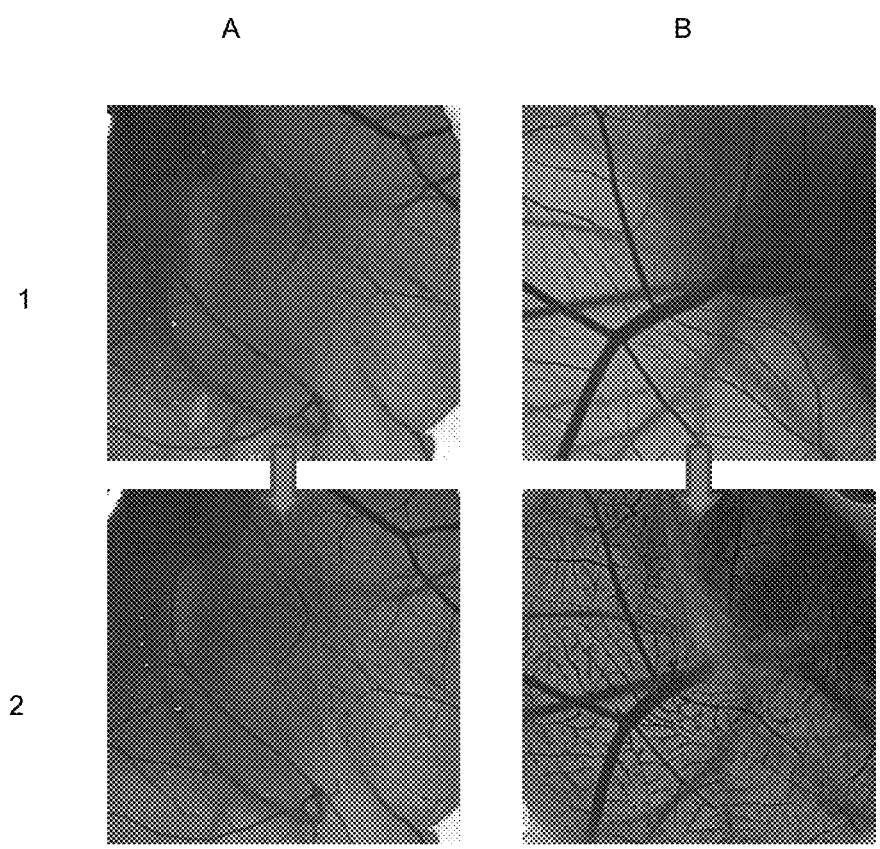

OIL-IN-WATER NANOEMULSION COMPOSITION OF CLOBETASOL

The present invention relates to the field of pharmacy. In particular, it relates to compositions containing clobetasol. More particularly, the present invention relates to oil-in-water nanoemulsion compositions of clobetasol, processes for their preparation, as well as their use as a medicament and particularly in the prophylaxis and/or treatment of inflammatory diseases or conditions.

BACKGROUND ART

Clobetasol propionate is the International Nonproprietary Name (INN) of [17-(2-chloroacetyl)-9-fluoro-11-hydroxy-10,13,16-trimethyl-3-oxo-6,7,8,11,12,14,15,16-octahydro-cyclopenta[a]phenanthren-17-yl] propanoate having the CAS number 25122-46-7. The structure of clobetasol propionate corresponds to the formula (I):

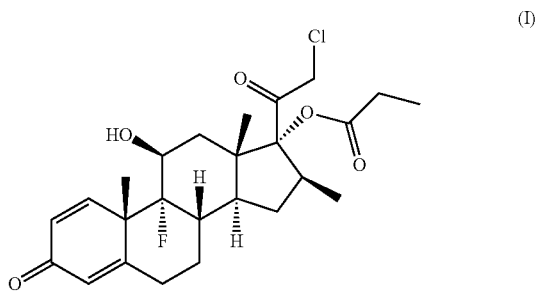

Clobetasol propionate is a corticosteroid of the glucocorticoid class used for the treatment of various inflammatory diseases.

On one hand, clobetasol propionate is used for the treatment of skin disorders including eczema, herpes labialis, psoriasis, and lichen sclerosus. It is also used to treat several auto-immune diseases including alopecia areata, vitiligo, lichen planus (auto immune skin nodules), and mycosis fungoides (T-cell skin lymphoma). It has very high potency and typically should not be used with occlusive dressings, or for extended continuous use. It can be in form of topical formulations such as shampoo, mousse, ointment and emollient cream presentations.

On the other hand, it has been also disclosed that clobetasol propionate exhibit a strong anti-inflammatory action and therefore, useful in the form of an eye drops for the treatments of various ocular diseases, for instance, inflammatory diseases of external- and anterior-ocular sites such as blepharitis, conjunctivitis, keratitis, scleritis, episcleritis, iritis, iridocyclitis and uveitis as well as inflammatory diseases developed after ocular operations.

However, due to the low solubility in water of clobetasol propionate, it is difficult to prepare stable compositions containing clobetasol propionate without compromising its pharmacokinetic and pharmacodynamics properties.

Even though such difficulty of obtaining formulation of clobetasol propionate, there are some formulations containing clobetasol propionate in the state of the art. Particularly, the European patent number EP0844001 discloses an oil-in-water emulsion of clobetasol propionate comprising liquid paraffin oil and a phospholipid for being instilled in the eye.

The emulsions have well recognized limitations for ocular administration, as blurred vision or lack of patient compliance due to the viscosity of formulations. In particular, these emulsions have limited bioavailability and permeability Thus, the ocular bioavailability following topical administration of emulsions to the eye remains a challenge still not satisfactorily resolved.

Furthermore, an additional constrain for the ocular compositions is their sterilization. It is disclosed in the state of the art several techniques to sterilizate ocular compositions that involve thermic or radiation procedures that may impact on clobetasol stability. In particular, the compositions disclosed in the European patent number EP0844001 requires a complex manufacturing process to get an uniform distribution of active ingredient that may compromise the stability of the drug substance, even more for a highly sensitive molecule like clobetasol.

Besides, the PCT patent application WO2017037663 discloses a topical oil-in-water nanoemulsion of clobetasol propionate for the treatment of psoriasis, wherein the composition comprises a high amount of alcohols, oil components and surfactants. The compositions disclosed in this patent application still have problems of non-appropriate tolerability in ocular or mucous membranes due to high proportion of solvents or non-suitable components for those routes of administration. Furthermore, the method for obtaining such compositions requires high energy methods that impair the stability behaviour of the drug. Finally, the PCT patent application WO2017037663 is silent about the release of the active ingredient from the composition and the related activity is not demonstrated.

Thus, from what is known in the art, there is still room of finding stable compositions containing clobetasol propionate having appropriate pharmacokinetic and pharmacodynamics properties as well as appropriate tolerability after its application.

SUMMARY OF INVENTION

Inventors have found a stable oil-in-water nanoemulsion composition containing clobetasol and having a low content of oil components and surfactants as well as a specific weight ratio between the oil component or the surfactant in relation to the amount of the active ingredient and a specific weight ratio between the amount of oils in relation to the sum of oil components and surfactants which allows having a good feeling after application and also appropriate pharmacokinetic and pharmacodynamics properties for the prophylaxis and/or treatment of inflammatory diseases or conditions.

On one hand, the nanoemulsion composition of the invention has good stability, even a good stability of the active ingredient or the final composition. On the other hand, the nanoemulsion composition of the invention also permits a good release and absorption of the effective amount of clobetasol to the treatment area with less side effects associated to an unduly distribution of clobetasol. And, finally, the nanoemulsion of the invention has also a comfortable feeling and tolerability after administration.

Thus, a first aspect of the invention relates to an oil-in-water nanoemulsion composition having a continuous aqueous phase and dispersed oil droplets, wherein the nanoemulsion comprises: (a) a therapeutically effective amount of clobetasol or a pharmaceutically acceptable salt or ester thereof; (b) one or more oil components; and (c) one or more surfactants; together with one or more pharmaceutically acceptable excipients or carriers wherein: the osmolality of the nanoemulsion composition is comprised from 100 mOsm/Kg to 500 mOsm/Kg; the droplet average size measured by Dynamic light scattering is comprised from 1 nm to 500 nm; the weight ratio between the oil components and the sum of the oil components and one or more surfactants is comprised from 0.001 to 0.5; the weight ratio between the oil component and clobetasol or a pharmaceutically acceptable salt or ester thereof is comprised from 1:1 to 200:1; and the weight ratio between the surfactant and clobetasol or a pharmaceutically acceptable salt or ester thereof is comprised from 2:1 to 200:1.

A second aspect of the invention relates to a process for the preparation of the oil-in-water nanoemulsion composition as defined in the first aspect of the invention, which comprises: (a) preparing the oil phase by mixing clobetasol with the oil components and the surfactants; (b) preparing the aqueous phase; (c) emulsifying the oil phase obtained in step (a) in the aqueous phase obtained in step (b); (d) optionally, adjusting the pH; the osmolality; the pH and the osmolality after step (a), step (b) or step (c); and (e) optionally, adding one or more additional pharmaceutically acceptable excipients or carriers in step (a), step (b) or step (c).

A third aspect of the invention relates to an oil-in-water nanoemulsion composition as defined in the first aspect of the invention, for use as a medicament.

And, the fourth aspect of the invention relates to an oil-in-water nanoemulsion composition as defined in the first aspect of the invention, for use in the prophylaxis and/or treatment of an inflammatory diseases or conditions.

BRIEF DESCRIPTION OF DRAWINGS

FIG. 1 shows the images obtained after performing the HET-Cam ocular irritation assay of the composition 11 of the present invention (A) and of the comparative composition 34 outside the scope of the present invention (B). The images were done at the initial time of the assay (1) and at the end of the assay (2) (5 minutes).

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range.

The term "clobetasol" used herein in the application refers to a compound of formula (II).

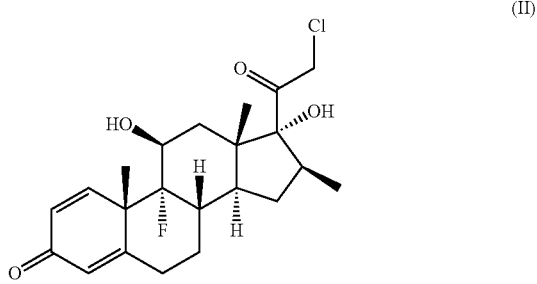

(II)

Clobetasol can be in form of a salt or in form of an ester. Particularly, the clobetasol can be in form of its propionate ester corresponding to the compound of formula (I) as defined above.

The term "nanoemulsion" refers to a colloidal dispersed system comprising at least two immiscible phases, one phase dispersed in the other phase as droplet having an average size measured by Dynamic light scattering from 1 nm to 500 nm.

The terms "average size" and "mean size" have the same meaning and are used interchangeable. They refer to average diameter of the droplets. The average size of these systems can be measured by standard processes known by persons skilled in the art. By "average size" and "mean size" is understood a D(n,50) droplet average size in number. The D(n,50) droplet average size is the median diameter, where 50% of the droplets are composed of droplets larger than the stated value, and 50% of the droplets are composed of droplets smaller than the stated value. In the present invention, the measurement of the average size of the droplets was performed by dynamic light scattering (DLS). DLS makes use of two common characteristics of colloids, the Tyndall effect (scattering) and the Brownian motion which cause light to be scattered at different intensities. Analyses of the time depend on the intensity fluctuations using mathematical models, allows the determination of the average size (cf. Hassan, P. et al, "Making sense of Brownian motion: colloid characterization by dynamic light scattering", Langmuir, 2015, vol. 31, pp. 3-12). The droplets are constantly moving due to Brownian motion and the relationship between the size of a droplets and its speed due to Brownian motion is defined in the Stokes-Einstein equation. As the droplets move around, the scattered light will cause intensity fluctuations. Furthermore, the signal intensity is compared at different times with itself in order to obtain the correlation function. This information can then be used to calculate the size distribution by intensity and it can be converted to a volume or a number size distribution. Particularly, the diameter of the droplets (i.e. the mean size of the droplets) is determined using a Zetasizer Nano ZS (Malvern Instruments). In the present invention the measurement of the average size (D(n,50)) of the droplets was directly measured (without dilution) by dynamic light scattering (DLS) with Zetasizer Nano ZS (Malvern Instruments) performing the calculations explained above in the present application.

The nanoemulsion composition of the invention is an oil-in-water nanoemulsion. The terms "oil-in-water" and "O/W" have the same meaning and are used interchangeable. They refer to a nanoemulsion wherein oil is dispersed as droplets throughout the aqueous phase.

The terms "percentage (%) by weight", "weight/weight %" and "w/w %" have the same meaning and are used interchangeable. They refer to the weight of each ingredient of the composition in relation to the total weight of the composition.

The terms "percentage (%) by volume", "volume/volume %" and "v/v %" have the same meaning and are used interchangeable. They refer to the volume each ingredient of the composition in relation to the total volume of the composition.

The terms "% (w/v)" and "mass concentration" have the same meaning and are used interchangeable. They refer to the mass of a ingredient divided by the volume of the composition.

The term "weight ratio" refers to the relation in weight of a given compound to another given compound, for instance, between the oil component and clobetasol.

The term "volume ratio" refers to the relation in volume of a given compound to another given compound, for instance, between the acetonitrile and water in the comparative buffered solution samples.

The term "osmolality" refers to the moles of solute that contribute to a solution's osmotic pressure (or osmoles) per kilogram of solvent. The osmolality is determined by the measurement of the freezing point depression of the sample using an osmometer.

The term "pH" is defined as the value given by a suitable, properly standardized, potentiometric sensor and measuring system. The measuring system has traditionally been referred to as the "pH meter". The pH of the nanoemulsions are measured by compendial traditional methods.

As it is mentioned above, the first aspect of the invention relates to an oil-in-water nanoemulsion comprising a therapeutically effective amount of clobetasol or a pharmaceutically acceptable salt or ester thereof. The expression "therapeutically effective amount" as used herein, refers to the amount of clobetasol or a pharmaceutically acceptable salt or ester thereof that, when administered, is sufficient to prevent development of, or alleviate to some extent, one or more of the symptoms of the disease or condition which is addressed. The particular dose of clobetasol administered according to this invention will of course be determined by the particular circumstances surrounding the case, including the active clobetasol administered, the route of administration, the particular condition being treated, and similar considerations.

In an embodiment, the clobetasol is in form of a pharmaceutically acceptable salt. The term "pharmaceutically acceptable salt" used herein encompasses a salt formed from pharmaceutically acceptable non-toxic acids including inorganic or organic acids. There is no limitation regarding the salts, except that if used for therapeutic purposes, they must be pharmaceutically acceptable. Salts of clobetasol may be prepared from pharmaceutically acceptable non-toxic acids, including inorganic and organic acids. Such acids include among others acetic, benzene sulfonic, benzoic, camphor sulfonic, citric, ethansulfonic, fumaric, gluconic, glutamic, hydrobromic, hydrochloric, lactic, maleic, malic, mandelic, methanesulfonic, phosphoric, succinic, sulphuric, tartaric, and p-toluensulfonic acid.

In an embodiment, the clobetasol is in form of a pharmaceutically acceptable ester. The term "pharmaceutically acceptable ester" used herein encompasses an ester formed from pharmaceutically acceptable non-toxic acids including inorganic or organic acids. There is no limitation regarding the ester, except that if used for therapeutic purposes, they must be pharmaceutically acceptable. Esters of clobetasol may be prepared from pharmaceutically acceptable non-toxic acids, including inorganic and organic acids. Such acids include among others acetic, butyric, propionic, benzenesulfonic, benzoic, camphorsulfonic, citric, ethansulfonic, fumaric, gluconic, glutamic, hydrobromic, hydrochloric, lactic, maleic, malic, mandelic, methanesulphonic, phosphoric, succinic, sulphuric, tartaric and p-toluensulphonic acid. In an embodiment, the clobetasol is in form of ester selected from the group consisting of clobetasol butyrate and clobetasol propionate; preferably clobetasol propionate of formula (I).

In an embodiment, the composition of the invention is one wherein the therapeutically effective amount of clobetasol is comprised from 0.001% to 0.1% by weight, preferably comprised from 0.01% to 0.05% by weight; more preferably 0.05% by weight. In an embodiment, the composition is one comprising from 0.001% to 0.1% by weight of clobetasol propionate; preferably comprised from 0.01% to 0.05% by weight of clobetasol propionate.

The term "oil" is used herein in a general sense to identify a wide class of substances typically unctuous, viscous and liquid at room temperature. Oil as here in defined can be from animal, mineral, vegetable or synthetic origin. The term "oil component" refers to oil, or a combination of multiple oils in a colloidal dispersion. The term "room temperature" refers to a temperature of the environment, without heating or cooling, and is generally from 20° C. to 25° C.

In an embodiment, the oil component of the nanoemulsion of the present invention is a ($C_4$-$C_{20}$) alkyl ester of monoglyceride, diglyceride, or triglyceride and mixture thereof. In an embodiment, the ($C_4$-$C_{20}$) alkyl ester of monoglyceride, diglyceride or triglyceride is medium chain triglycerides. The term "Medium chain triglycerides" and "MCT" have the same meaning and are used interchangeable and refers to triesters of glycerin and ($C_6$-$C_{12}$) fatty acids. Examples of MCTs include caproic acid ($C_6$), caprylic acid ($C_8$), capric acid ($C_{10}$) and lauric acid ($C_{12}$). The three fatty acid residues of the MCT can be the same or different, preferably there are two different fatty acid residues. In an embodiment, the oil is a medium chain triglyceride selected from caproic acid, caprylic acid, capric acid, lauric acid and mixture thereof; preferably the oil is a caprylic/capric acid triglyceride. The nanoemulsion compositions of the invention which comprise MCT as oil component are especially advantageous because the solubility of clobetasol in MCT is very high, and then the use of MCT allows the reduction of oil content in the nanoemulsion of the invention.

In an alternative embodiment, the oil component of the nanoemulsion of the present invention is other than monoglyceride, diglyceride or triglyceride esters, selected from the group consisting of ethyl oleate, decyl oleate, isopropyl myristate, isopropyl palmitate, isopropyl isostearate, isostearyl isostearate, glyceryl monosterate, myristyl lactate, ethylhexyl hydroxystearate, ethylhexyl pelargonate, triethylhexanoin, isohexadecane, light mineral oil, mineral oil, vegetable oil, triisononanoin, ($C_{12}$-$C_{15}$) alkyl benzoate, and mixtures thereof; preferably, selected from the group consisting of ethyl oleate, isopropyl myristate, isopropyl palmitate, isopropyl isostearate, isostearyl isostearate, decyl oleate, castor oil, argan oil, triisononanoin, ($C_{12}$-$C_{15}$) alkyl benzoate, and mixtures thereof.

The term "alkyl" refers to a saturated, branched or linear alkyl chain which contains the number of carbon atoms specified in the description or claims.

The term "vegetable oil" refers to a triglyceride extracted from a plant. Examples of vegetable oils are argan oil, corn oil, palm oil, coconut oil, cottonseed oil, olive oil, peanut oil, rapeseed oil, sunflower oil, sesame oil, soybean oil, safflower oil, castor oil, olive oil, and mixture thereof.

In an embodiment, the oil component is a mixture of a ($C_6$-$C_{12}$) alkyl ester of monoglyceride, diglyceride, or triglyceride and an oil other than monoglyceride, diglyceride or triglyceride esters as defined above. In an embodiment, the oil is a mixture of MCTs and castor oil.

As it is mentioned above, the weight ratio between the oil component and clobetasol or a pharmaceutically acceptable salt or ester thereof is comprised from 1:1 to 200:1. In an embodiment, the weight ratio between the oil component and clobetasol or a pharmaceutically acceptable salt or ester thereof is comprised from 1:1 to 100:1; preferably comprised from 1:1 to 90:1.

The term "surfactant", as used herein, refers to a compound that lowers the surface tension or interfacial tension between two liquids or between a liquid and a solid. Surfactants have a hydrophobic part and a hydrophilic part. Depending on the nature of the hydrophilic part the surfactants are classified as non-ionic (surfactant with a non-charged but polar hydrophilic part), anionic (when the hydrophilic part contains a negatively charged group), cationic (when the hydrophilic part contains a positively charged group) or amphoteric (when the when the hydrophilic part contains has both cationic and anionic groups).

In an embodiment, the one or more surfactants of the nanoemulsion of the present invention are non-ionic surfactants. Examples of non-ionic surfactants include, but are not limited to, ($C_{30}$-$C_{40}$)alkyl poly(ethylene oxide), block copolymers of poly(ethylene oxide) and poly(propylene oxide) (commercially called Poloxamers or Poloxamines), ($C_8$-$C_{14}$)alkyl polyglucosides including octyl glucoside and decyl maltoside, fatty alcohols including cetyl alcohol and oleyl alcohol, cocamide MEA, cocamide DEA, sorbitan esters and derivatives thereof or sorbitan esters ethoxylate and derivatives thereof.

In an embodiment, the one or more surfactant of the nanoemulsion of the present invention is a non-ionic surfactant selected from the group consisting of polyoxyl castor oil with 30 to 40 oxyethylene units, in particular polyoxyl 35 castor oil (also known as polyethylene glycol 35 castor oil; marketed as Kolliphor® EL, Cremophor® EL), polyoxyl hydrogenated castor oil with 40 to 60 oxyethylene units, in particular polyoxyl 40 hydrogenated castor oil (also known as polyethylene glycol 40 hydrogenated castor oil; marketed as Cremophor® RH40), polyoxyethylene 20 sorbitan monooleate (also known as polysorbate 80 and marketed as Tween® 80), polyoxyethylene 20 sorbitan monostearate (also known as polysorbate 60 and marketed as Tween® 60), polyoxyethylene 20 sorbitan trioleate (also known as polysorbate 85 marketed as Tween® 85), polyoxyethylene 20 sorbitan tristearate (also known as polysorbate 65 marketed as Tween® 65), polyoxyethylene 20 sorbitan monolaurate (also known as polysorbate 20), polyoxyethylene 20 sorbitan monopalmitate (also known as polysorbate 40), polyoxyethylene 4 sorbitan monolaurate (also known as polysorbate 21 and marketed as Tween® 21), sorbitan trioleate (marketed as Span®85), sorbitan tristearate, sorbitan sesquioleate, sorbitan oleate (marketed as Span®80), sorbitan stearate, sorbitan isostearate, sorbitan palmitate, sorbitan laurate (marketed as Span®20), polyethylene glycol hexadecyl ether (marketed as Brij® C10), glyceryl stearate (marketed as Cithrol® GMS40), glyceryl monooleate, glycol stearate, glycol distearate, D-α-Tocopherol polyethylene glycol 1000 succinate (TPGS), polyoxyl steraryl ether with 2 oxyethylene units, polyoxyl castor oil with 2 to 20 oxyethylene units, cetostearyl alcohol, stearyl alcohol, oleth-2, nonoxynol, octoxynol, octylphenol polymethylene, polyoxyl 40 stearate, poly(ethylene oxide)-poly(propylene oxide) copolymers (in particular poloxamer 188 and poloxamer 407) and mixtures thereof.

In an embodiment, the one or more surfactant of the nanoemulsion of the present invention is a non-ionic surfactant selected from the group consisting of polyoxyl 35 castor oil, polyoxyl 40 hydrogenated castor oil, polyoxyethylene 20 sorbitan monooleate, polyoxyethylene 20 sorbitan monostearate polyoxyethylene 20 sorbitan trioleate, polyoxyethylene 20 sorbitan monolaurate, polyoxyethylene 20 sorbitan tristearate, polyoxyethylene 20 sorbitan monopalmitate, polyethylene glycol hexadecyl ether, glyceryl stearate, D-α-Tocopherol polyethylene glycol 1000 succinate (TPGS), poloxamer 188, poloxamer 407, polyoxy 40 stearate, sorbitan monolaurate, octoxynol 40 and mixtures thereof. In an embodiment, the one or more surfactant of the nanoemulsion of the present invention is a non-ionic surfactant selected from the group consisting polyoxyethylene 20 sorbitan monooleate and polyoxyl 35 castor oil.

In an embodiment, the one or more surfactant of the nanoemulsion of the present invention is a non-ionic surfactant selected from the group consisting of sorbitan esters ethoxylates derivatives, sorbitan esters derivatives, poly (ethylene oxide)-poly(propylene oxide) copolymers, polyoxyl 35 castor oil, polyoxyl 40 hydrogenated castor oil, polyoxyl 40 stearate, octoxynol 40, D-α-Tocopherol polyethylene glycol 1000 succinate (TPGS), and mixtures thereof.

As it is mentioned above, the weight ratio between the surfactant and clobetasol or a pharmaceutically acceptable salt or ester thereof is comprised from 2:1 to 200:1. In an embodiment, the weight ratio between the surfactant and clobetasol or a pharmaceutically acceptable salt or ester thereof is comprised from 2:1 to 190:1; preferably comprised from 2:1 to 180:1.

As it is also mentioned above, the nanoemulsion of the invention has a weight ratio between the oil components and the sum of the oil components and the one or more surfactants comprised from 0.001 to 0.5. In an embodiment, the weight ratio between the oil components and the sum of the oil components and the surfactants is comprised from 0.001 to 0.4; preferably comprised from 0.005 to 0.4; more preferably comprised from 0.005 to 0.3.

In an embodiment, the nanoemulsion of the invention has an osmolality comprised from 100 mOsm/Kg to 500 mOsm/kg; preferably comprised from 150 mOsm/Kg to 400 mOsm/kg. In an embodiment, when the nanoemulsion of the invention is an ophthalmic composition then the osmolality is comprised from 120 mOsm/Kg to 380 mOsm/Kg. It is advantageous because these compositions are isotonic and hence suitable for ocular administration.

In an embodiment, the nanoemulsion of the invention has a droplet average size comprised from 1 nm to 500 nm; preferably comprised from 1 nm to 250 nm. In an embodiment, when the nanoemulsion of the invention is an ophthalmic composition then the droplet average size measured by Dynamic light scattering is comprised from 1 nm to 250 nm. It is advantageous because the nanoemulsion composition is transparent and avoids the uncomfortable feeling of blurry vision.

In an embodiment, the nanoemulsion of the invention has a pH comprised from 4.0 to 8.0; preferably comprised from 4.5 to 7.4. In an embodiment, when the nanoemulsion of the invention is an ophthalmic composition then the pH of the composition comprises from 4.5 to 7.4 as the pH of tear fluid.

In an embodiment, the nanoemulsion of the invention has an amount of ethanol comprised from 0% to 3% by weight; preferably the amount of ethanol is comprised from 0% to 2% by weight. It is advantageous because the lower amount of ethanol allows reducing the uncomfortable feeling of use in ophthalmic, nasal or buccal administration routes.

As it is mentioned above, the nanoemulsion of the invention also comprises one or more pharmaceutically acceptable excipients or carriers. The terms "acceptable excipients or carriers" refers to acceptable material, composition or vehicle, which include without limitation pH adjusting agents, preservatives, antioxidants, chelating agents, stabilizers, viscosizing agents, adhesive polymers, penetration enhancers and tonicity agents. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

In an embodiment, the nanoemulsion of the invention further comprises one or more pH adjusting agents. The term "pH adjusting agent" refers to acids or bases or their mixtures that can be used to adjust the pH of the finished product to the desired level, without affecting the stability of the emulsion. In an embodiment, the nanoemulsion of the invention further comprises a pH adjusting agent selected from the group consisting of lactic acid and salts thereof (such as sodium lactate, potassium lactate and calcium lactate), citric acid and salts thereof (such as sodium citrate, potassium citrate, calcium citrate, lithium citrate, trisodium citrate and disodium hydrogen citrate), tartaric acid and salts thereof (such as sodium tartrate potassium tartrate, calcium tartrate and lithium tartrate), acetic acid and salts thereof (such as sodium acetate, potassium acetate and calcium acetate), hydrochloric acid, boric acid and salts thereof (sodium borate), sulphuric acid and salts thereof (such as sodium sulphate and potassium sulphate), nitric acid, hydrochloric acid, phosphoric acid and salts thereof (such as sodium dihydrogen phosphate, sodium monohydrogen phosphate, potassium dihidrogen phosphate lithium phosphate, potassium phosphate and calcium phosphate), carbonic acid and salts thereof (such as sodium carbonate, sodium hydrogen carbonate and potassium hydrogen carbonate), maleic acid and salts thereof (lithium maleate, sodium maleate, potassium maleate and calcium maleate), succinic acid and salts thereof (lithium succinate, sodium succinate, potassium succinate and calcium succinate), sodium hydroxide, potassium hydroxide, triethanolamine, diisopropanolamine, ammonia, tris(hydroxymethyl)aminomethane, tris(hydroxymethyl)aminomethane hydrochloride, and mixtures thereof. In an embodiment, the pH adjusting agent is selected from the group consisting of tris(hydroxymethyl)aminomethane, tris(hydroxymethyl)aminomethane hydrochloride, potassium dihydrogen phosphate, disodium hydrogen phosphate and mixtures thereof.

In an embodiment, the nanoemulsion of the invention further comprises a pH adjusting agent selected from the group consisting of acetic acid, boric acid, sorbic acid, citric acid, phosphoric acid, sodium phosphate, dibasic sodium phosphate, monobasic sodium phosphate, potassium dihydrogen phosphate and salts thereof, hydrochloric acid, sodium hydroxide, sodium thiosulfate, sodium sulfite, sodium sulphate, tris(hydroxymethyl)aminomethane, tris(hydroxymethyl)aminomethane hydrochloride, sodium hydrogen carbonate, sodium borate, sodium acetate, sodium bisulphate, sodium benzoate, sodium citrate and mixtures thereof.

In a preferred embodiment, the pH adjusting agent is tris(hydroxymethyl)aminomethane and salts thereof. The amount of the pH adjusting agent in the nanoemulsion of the present invention is comprised from 0.01% to 3% by weight.

In an embodiment, the nanoemulsion of the invention further comprises one or more stabilizers. The term "stabilizer" refers to a compound that enhanced the stability of the nanoemulsion and/or of the active ingredient. In an embodiment, the stabilizer is a water soluble polymer for instance polyvinylpyrrolidone, polyvinyl alcohol, hydroxyethylcellulose, hydroxypropylcellulose, methylcellulose, hydroxypropylmethylcellulose, carboxymethylcellulose, salt thereof, and mixture thereof; preferably polyvinylpyrrolidone. In an embodiment, the stabilizer is tris(hydroxymethyl)aminomethane and or tris(hydroxymethyl)aminomethane hydrochloride. The use of the tris(hydroxymethyl)aminomethane and salts thereof is especially advantageous because allows a reduction in the total amount of degradation products, which means that the stability of the active ingredient in the nanoemulsion of the invention is higher than in the emulsions disclosed in the state of the art. The amount of the stabilizer in the nanoemulsion of the present invention is comprised from 0.01% to 15% by weight.

In an embodiment, the nanoemulsion of the invention further comprises one or more bioadhesive polymers. The term "bioadhesive polymers" refers to a substance which can increase residence time of the compositions of the invention. Examples of bioadhesive polymers appropriate for the present invention include polyvinylpirrolidones, such as Povidone K 17, Povidone K25, Povidone K 30 and Povidone K 90F; polyvinyl alcohol; xanthan gum; guar gum; welan gum; gellan gum; tragacanth gum; ceratonia gum; agar; methylcellulose; ethylcellulose; hydroxyethyl cellulose; hydroxyethylmethyl cellulose; hydroxypropyl cellulose; hydroxypropylmethyl cellulose; hydroxypropylmethyl cellulose phthalate; hydroxypropylmethyl cellulose acetate succinate; sodium carboxymethylcellulose; calcium carboxymethylcellulose; polyethylene glycol; glycerine; carrageenan; alginic acid; sodium alginate; potassium alginate; propylene glycol alginate; hyaluronic acid; sodium hyaluronate; poly(acrylic acid) derivatives such as carbomer and polycarbol; poloxamers; chitosan and chitosan derivatives; vinyl methyl ether/maleic anhydride copolymers; maltodextrin; and mixtures thereof. In an embodiment, the compositions of the invention comprise polyvinylpyrrolidone as bioadhesive polymer. In an embodiment, the bioadhesive polymer is present in an amount of from 0.01% to 15% by weight with respect to the total weight of the compositions.

In an embodiment, the nanoemulsion of the invention further comprises one or more preservatives. The term "preservative" refers to a compound that preserve from microbial and/or fungal contaminations. Examples of preservatives appropriate for the present invention include but is not limited to benzalkonium chloride, cetalkonium chloride, bezethonium chloride, chlorhexidine, benzyl alcohol, chlorobutanol, 2-phenylethanol, propylparaben, methylparaben, phenylmercuric acetate, phenylmercuric borate, sodium dehydroacetate, sorbic acid phenylmercuric nitrate, cetyl pyridinium chloride, cetrimonium bromide, benzyl bromide, sodium perborate, thimerosal and mixture thereof. The amount of the preservative in the nanoemulsion of the present invention is comprised from 0% to 1% by weight.

In an embodiment, the nanoemulsion of the invention further comprises one or more tonicity agent. The term "tonicity agent" refers to a compound that can be used for adjusting the osmolality of the nanoemulsion. In an embodiment, the tonicity agent is selected from the group consisting of sodium chloride, potassium chloride, calcium chloride, sodium phosphate, potassium phosphate, sodium hydrogen carbonate, calcium carbonate, sodium lactate, sorbitol, mannitol, xylitol, dextrose, polyethylene glycol, propylene glycol, dextran, and mixture thereof; preferably glycerin. The amount of the tonicity agent in the nanoemulsion of the present invention is comprised from 0% to 15 by weight.

In an embodiment, the nanoemulsion of the invention further comprises one or more chelating agent. The term "chelating agent" and "chelant" have the same meaning and are used interchangeable. They refer to a compound that is capable of complexing ions. Examples of chelating agents are citric acid, in particular citric acid monohydrate, EDTA (ethylenediaminetetraacetic acid) and its salts, such as dipotassium EDTA, disodium EDTA, calcium disodium EDTA, sodium EDTA and trisodium EDTA, fumaric acid, malic acid and maltol. In an embodiment, the chelating agent is selected from the group consisting of sodium edetate, citric acid, and salt and mixture thereof. The amount of the chelating agent in the nanoemulsion of the present invention is comprised from 0% to 2 by weight.

The term "penetration enhancer", as used herein, refers to a substance which enhances drug penetration. Examples of penetration enhancers are surfactants such as sorbitan monolaurate, sorbitan monopalmitate, sorbitan trioleate, polyoxyethylene 20 sorbitan monolaurate, polyoxyethylene 20 sorbitan monopalmitate, polyoxyethylene 5 sorbitan monooleate, polyoxyethylene 20 sorbitan trioleate, polyoxyethylene 9 lauryl ether, polyoxyethylene 23 lauryl ether, polyoxyethylene 20 cetyl ether, polyoxyethylene 20 oleyl ether, polyethylene glycol octadecyl ether, polyoxyethylene 40 stearate, polyoxyethylene 50 stearate, palmitoyl carnitine, sodium caprate, sodium dodecyl sulfate, bile acids such as deoxycholic acid, taurocholic acid, taurodeoxycholic acid, urodeoxycholic acid, and tauroursodeoxycholic acid, fatty acids such as capric acid, caprylic and oleic acid, lauralkonium chloride, benzalkonium chloride, cetalkonium chloride, cetrimonium bromide, chlorhexidine digluconate, benzyl alcohol, chlorbutanol, 2-phenylethanol, paraben, propyl paraben and methyl paraben, EDTA, 1-dodecylazacycloheptan-2-one (Azone), hexamethylene lauramide, hexamethylene octanamide, decylmethylsulfoxide, saponin, cyclodextrins, pz-peptide, α-amino acid, cetylpyridinium chloride, cytochalasins, ionophores or mixtures thereof. The amount of the penetration enhancer in the nanoemulsion of the present invention is comprised from 0.01% to 10% by weight.

In an embodiment, the nanoemulsion of the present invention comprises: from 0.001% to 0.1% by weight of clobetasol or a pharmaceutically acceptable salt or ester thereof; preferably clobetasol propionate; from 0.001% to 20% by weight of one or more oil components; from 0.002% to 20% by weight of one or more surfactants; water in a sufficient amount for 100%; and optionally, a pH adjusting agent in a sufficient amount for having a pH comprised from 4.0 to 8.0; and optionally, an tonicity agent in a sufficient amount for having an osmolality comprised from 100 mOsm/kg to 500 mOsm/Kg.

In an embodiment, the nanoemulsion of the present invention comprises: from 0.01% to 0.05% by weight of clobetasol pharmaceutically acceptable salt or ester thereof; clobetasol propionate; from 0.01% to 10% by weight of one or more oil components; from 0.02% to 10% by weight of one or more surfactants; water in a sufficient amount for 100%; and optionally, a pH adjusting agent in a sufficient amount for having a pH comprised from 4.0 to 8.0; and optionally, an tonicity agent in a sufficient amount for having an osmolality comprised from 100 mOsm/Kg to 500 mOsm/Kg.

In an embodiment, the nanoemulsion of the present invention comprises: from 0.001% to 0.1% by weight of clobetasol or a pharmaceutically acceptable salt or ester thereof; preferably clobetasol propionate; from 0.001% to 20% by weight of medium chain fatty acid triglyceride; from 0.002% to 20% by weight of polyoxyethylene 20 sorbitan monooleate; water in a sufficient amount for 100 mL; optionally, tris(hydroxymethyl)aminomethane in a sufficient quantity for having a pH comprised from 4.0 to 8.0; and optionally, glycerine in a sufficient quantity for an osmolality comprised from 100 mOsm/Kg to 500 mOsm/Kg.

In an embodiment, the nanoemulsion of the present invention comprises: from 0.01% to 0.05% by weight of clobetasol or a pharmaceutically acceptable salt or ester thereof; preferably clobetasol propionate; from 0.01% to 10% by weight of medium chain fatty acid triglyceride; from 0.02% to 10% by weight of polyoxyethylene 20 sorbitan monooleate; water in a sufficient amount for 100 mL; optionally, tris(hydroxymethyl)aminomethane in a sufficient quantity for having a pH comprised from 4.0 to 8.0; and optionally, glycerine in a sufficient quantity for an osmolality comprised from 100 mOsm/Kg to 500 mOsm/Kg.

In an embodiment, the nanoemulsion composition of the invention is an ophthalmic composition, otic composition, nasal composition or buccal composition. In an embodiment, the nanoemulsion composition of the invention is in form of eye drops, ear drops, nose drops or oral spray.

In an embodiment, the nanoemulsion composition is an ophthalmic composition which is in form of eye drops. It is advantageous because the nanoemulsion of the present invention is transparent avoiding uncomfortable feeling after use such as blurry vision and burning. When the nanoemulsion is an ophthalmic composition it should be sterile. The term "sterile" refers to a nanoemulsion composition that has been aseptically processed and that is devoid of viable bacteria, fungi or other microorganisms. In an embodiment, the nanoemulsion composition is a sterile ophthalmic composition.

In an embodiment, the nanoemulsion composition is a multi-dose ophthalmic composition and the composition further comprises a preservative as defined above. In an embodiment, the nanoemulsion composition is a uni-dose ophthalmic composition. It is advantageous because these nanoemulsions do not require the inclusion in the composition of preservatives.

The second aspect of the invention relates to a process for the preparation of the nanoemulsion as defined above. The nanoemulsion compositions of the present invention can be prepared according to methods well known in the state of the art for the preparation of nanoemulsion, particularly to oil-in-water nanoemulsion. The appropriate excipients and/or carriers, and their amounts, can readily be determined by those skilled in the art according to the type of formulation being prepared.

In an embodiment, the process for the preparation of the nanoemulsions of the present invention is performed by phase inversion composition (PIC). In an embodiment, the process for the preparation of the oil-in-water nanoemulsion composition as defined above comprises: (a) preparing the oil phase by mixing clobetasol with the oil components and the surfactants; (b) preparing the aqueous phase; (c) emulsifying the oil phase obtained in step (a) in the aqueous phase obtained in step (b); (d) optionally, adjusting the pH; the osmolality; the pH and the osmolality after step (a), step (b) or step (c); and (e) optionally, adding one or more additional pharmaceutically acceptable excipients or carriers in step (a), step (b) or step (c).

In an embodiment, step (a) is performed by mixing in a suitable container until a homogenous mixture is obtained.

In an embodiment, step (b) is performed by dissolving or dispersing the components of the aqueous phase. In an embodiment, step (b) is performed for the appropriate period of time for having an homogenous blend.

In an embodiment, step (c) is performed by emulsifying the oil phase with the aqueous phase keeping a continuous mixing procedure at temperatures between 10° C. to 60° C. In an embodiment, step (c) is performed when the temperature of the oil phase obtained in step (a) is close to the temperature of the aqueous phase obtained in step (b). The expression "the temperature of the oil phase is close to the temperature of the aqueous phase" means that the temperature value is "approximate" due to the measurement error. It should be understood that "close" corresponds to a given temperature value±10° C. The variability of the values is due to the inherent sensibility of the method.

The nanoemulsion of the invention can be performed by a simple process under mild conditions and without the need of a homogenizing step at high pressure. Methods related to high energy procedures (for instance high pressure and ultrasounds) may negatively impact on shelf life of active ingredient and the stability of the final dosage form. Therefore, the process for preparing the nanoemulsion of the present invention is advantageous for the stability of the active ingredient.

In an embodiment, when the nanoemulsion composition is a sterile composition then the process as defined above further comprises a sterilization step. In an embodiment, the sterilization step is performed after step (a); step (b); step (c); step (d) or step (e). In an embodiment, the sterilization process is performed after step (e). The sterilization step can be performed according to methods well known in the state of the art. In an embodiment, the sterilization step is performed by a method selected from the group consisting of filtration, autoclaving, heating, irradiation, and combination thereof; preferably the sterilization step is performed by filtration. In an embodiment, the process of the invention further comprises a sterilization filtration. Due to the droplet average size and its flexibility, the nanoemulsion may be sterilised by filtration, which is advantageous because of the use of mild conditions and without the need of high temperatures or radiation procedures that may negatively impact on the stability of the active ingredient. Therefore, the process for preparing the nanoemulsion of the present invention which involves the sterilization filtration is advantageous for the stability of the active ingredient and the nanoemulsion.

All the embodiments disclosed above for the nanoemulsion composition of the present invention also applies for the process for its preparation.

The nanoemulsion composition of the present invention may be defined by its preparation process as defined above and therefore, the nanoemulsion composition of the invention obtainable by the process of the invention is considered part of the invention. For the purposes of the invention the expressions "obtainable", "obtained" and equivalent expressions are used interchangeably, and in any case, the expression "obtainable" encompasses the expression "obtained".

All the embodiments disclosed above for the nanoemulsion composition of the present invention, as well as for the process for its preparation also apply for the nanoemulsion obtainable by the process for preparation.

The third aspect of the invention relates to a nanoemulsion composition as defined above for use as a medicament.

As mentioned above, the fourth aspect of the invention relates to a nanoemulsion composition as defined above for use in the prophylaxis and/or treatment of an inflammatory disease or condition. This aspect could be also formulated as the use of a nanoemulsion composition as defined above for the preparation of a medicament for the prophylaxis and/or treatment of an inflammatory disease or condition. It also relates to a method for the prophylaxis and/or treatment of a mammal suffering, or susceptible to suffer, from an inflammatory disease or condition, wherein the method comprises administering to said mammal the nanoemulsion composition as defined above which comprises a therapeutically effective amount of clobetasol or a pharmaceutically acceptable salt or ester thereof together with one or more pharmaceutically acceptable excipients or carriers.

In an embodiment, the inflammatory disease or condition is selected from the group consisting of ophthalmic inflammatory disease or condition, otological inflammatory disease or condition, and oropharyngeal inflammatory disease or condition.

In an embodiment, the inflammatory disease or condition is an ophthalmic inflammatory disease or condition. In an embodiment, the ophthalmic inflammatory disease or condition is selected from the group consisting of Inflammation and pain associated with post-ocular surgery; uveitis for instance anterior uveitis (iritis and iridocyclitis) or middle uveitis (Cyclitis); toxic anterior segment syndrome; glaucomatocyclitic crisis or hypertensive anterior uveitis for instance posner-Schlossman syndrome; sympathetic ophthalmia for instance bilateral granulomatous panuveitis secondary to intraocular surgery or penetrating wounds; autoimmune disease with ocular involvement for instance Cogan's syndrome or Reiter's syndrome; allergic conjunctivitis for instance seasonal allergic conjunctivitis, perennial allergic conjunctivitis, vernal keratoconjunctivitis and atopic keratoconjunctivitis; blepharitis; interstitial keratitis; marginal keratitis (catarrhal ulcer); bacterial, viral, or fungal conjunctivitis; and severe dry eye.

In an embodiment, the inflammatory disease or condition is an otological inflammatory disease or condition. In an embodiment, the otological inflammatory disease or condition is selected from the group consisting of external otitis for instance diffuse, localized or eczematous otitis; otitis media for instance acute or chronic; atopic dermatitis with ear canal involvement.

In an embodiment, the inflammatory disease or condition is an oropharyngeal inflammatory disease or condition. In an embodiment, the oropharyngeal inflammatory disease or condition is selected from the group consisting of pharyngitis; acute epiglotitis; allergic laryngitis; noninfectious acute laryngitis; lichen planus; aphthous stomatitis and pemphigoid.

All the embodiments disclosed above for the nanoemulsion composition of the present invention also applies for the nanoemulsion composition limited by its use.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. Oil-in-Water Nanoemulsions 1.1. Compositions
A. Compositions of the Invention Examples 1-22 illustrate nanoemulsions of the present invention which contain clobetasol propionate of formula (I).

Tables 1A-1C illustrates the quantitative composition of the nanoemulsion of Examples 1-22 following within the scope of the present invention, wherein the amount of the components is expressed in percentage (%) by weight of each ingredient in relation to the total weight of the composition. Besides, the osmolality of the nanoemulsions of Example 1-22 is comprised from 100 mOsm/Kg to 500 mOsm/Kg, the droplet average size measured by Dynamic light scattering is comprised from 1 nm to 500 nm and the pH is comprised from 4.0 to 8.0.

TABLE 1A

| Example | 1 | 2 | 3 | 4 | 5 | 6 | 7 |
|---|---|---|---|---|---|---|---|
| Clobetasol propionate | 0.010 | 0.101 | 0.050 | 0.050 | 0.051 | 0.050 | 0.050 |
| Polysorbate80 | — | — | — | — | — | 5.000 | — |
| Cremophor ®EL | 2.053 | 5.040 | 2.000 | 5.000 | 5.008 | — | 5.010 |
| Castor oil | 2.017 | 0.501 | — | — | — | — | 1.008 |
| Medium chain triglycerides | — | 1.514 | — | — | — | 0.500 | — |
| Triisononanoin | — | — | 0.104 | — | — | — | — |
| Isopropyl isostearate | — | — | — | 0.411 | — | — | — |
| Isopropyl myristate | — | — | — | — | 0.516 | — | — |
| Benzalkonium chloride | — | — | 0.020 | — | — | 0.010 | 0.010 |
| EDTA | — | — | 0.103 | — | — | 0.100 | 0.100 |
| Povidone | — | — | — | — | — | 5.002 | 5.010 |
| Sodium hidroxide 1N | — | 0.338 | — | — | — | 0.312 | — |
| Tris(hydroxymethyl)aminomethane hydrochloride | 0.839 | — | — | 0.860 | — | — | 0.661 |

TABLE 1A-continued

| Example | 1 | 2 | 3 | 4 | 5 | 6 | 7 |
|---|---|---|---|---|---|---|---|
| Tris(hydroxymethyl)aminomethane | 0.053 | — | — | 0.118 | — | — | 0.154 |
| Trisodium citrate dihydrate | — | 0.821 | — | — | — | 0.822 | — |
| Disodium hydrogen citrate sesquihydrate | — | 0.252 | — | — | — | 0.250 | — |
| Glycerin | 0.950 | — | 2.079 | — | 8.009 | 0.735 | 1.083 |
| Water | q.s* 100% | q.s* 100% | q.s* 100% | q.s* 100% | q.s* 100% | q.s* 100% | q.s* 100% |

"q.s." means quantity sufficient

TABLE 1B

| Example | 8 | 9 | 10 | 11 | 12 | 13 | 14 |
|---|---|---|---|---|---|---|---|
| Clobetasol propionate | 0.027 | 0.053 | 0.049 | 0.050 | 0.049 | 0.050 | 0.050 |
| Polysorbate80 | 4.507 | 5.035 | 5.034 | 5.002 | 4.942 | — | — |
| Span ®85 | 0.507 | — | — | — | — | — | — |
| Cremophor ®EL | — | — | — | — | 2.000 | 5.001 | 5.010 |
| Castor oil | — | — | — | — | 1.028 | 1.031 | 1.268 |
| Medium chain triglycerides | 0.505 | 0.503 | 0.509 | 0.502 | 0.548 | — | 1.270 |
| Benzalkonium chloride | 0.020 | — | 0.012 | 0.010 | — | 0.010 | — |
| EDTA | — | — | 0.100 | 0.100 | — | — | 0.052 |
| Povidone | — | — | 5.016 | 5.004 | — | — | — |
| Sodium hidroxide 1N | 4.901 | — | — | — | — | — | 5.131 |
| Citric acid | 0.500 | — | — | — | — | — | 0.502 |
| Tris(hydroxymethyl)aminomethane hydrochloride | — | — | 0.666 | 0.838 | — | 0.860 | — |
| Tris(hydroxymethyl)aminomethane | — | — | 0.147 | 0.053 | — | 0.116 | — |
| Mannitol | 0.182 | — | — | — | — | — | — |
| Sodium chloride | 0.545 | — | — | — | — | — | 0.607 |
| Glycerin | — | — | 0.648 | 0.884 | — | 1.109 | — |
| Water | q.s* 100% | q.s.* 100% | q.s.* 100% | q.s.* 100% | q.s.* 100% | q.s.* 100% | q.s.* 100% |

"q.s." means quantity sufficient

TABLE 1C

| Example | 15 | 16 | 17 | 18 | 19 | 20 | 21 | 22 |
|---|---|---|---|---|---|---|---|---|
| Clobetasol propionate | 0.102 | 0.050 | 0.050 | 0.050 | 0.030 | 0.010 | 0.050 | 0.050 |
| Polysorbate80 | 2.075 | 2.030 | 2.000 | 5.003 | 3.505 | 1.503 | 7.013 | 6.997 |
| Span ® 20 | — | — | — | — | 0.499 | — | — | — |
| Cremophor ®EL | 5.035 | 5.027 | 8.050 | — | — | — | — | — |
| Cremophor ®RH40 | — | — | — | — | — | 0.502 | — | — |
| Castor oil | 1.279 | 2.509 | 4.002 | — | — | 0.262 | — | — |
| Medium chain triglycerides | 1.302 | 2.498 | 4.038 | 0.500 | 0.401 | 0.256 | 0.501 | 0.501 |
| Benzalkonium chloride | — | — | — | 0.011 | 0.010 | 0.010 | 0.020 | 0.050 |
| EDTA | — | 0.050 | — | — | 0.010 | 0.010 | 0.101 | 0.202 |
| Povidone | 5.001 | — | — | — | 2.005 | 2.003 | 2.010 | 2.005 |
| Sodium hidroxide 1N | — | 5.064 | — | — | 6.175 | 4.791 | — | — |
| Citric acid | — | 0.500 | — | — | 0.501 | 0.402 | — | — |
| Tris(hydroxymethyl)aminomethane hydrochloride | — | — | — | 0.861 | — | — | 0.666 | 0.836 |
| Tris(hydroxymethyl)aminomethane | — | — | — | 0.119 | — | — | 0.150 | 0.054 |
| Mannitol | — | 0.203 | — | — | 0.202 | 0.501 | — | — |
| Sodium chloride | — | 0.500 | — | — | 0.500 | 0.654 | — | — |
| Glycerin | — | — | — | 1.097 | — | — | 0.678 | 1.000 |
| Water | q.s* 100% | q.s.* 100% | q.s.* 100% | q.s.* 100% | q.s.* 100% | q.s.* 100% | q.s.* 100% | q.s.* 100% |

"q.s." means quantity sufficient

B. Comparative Compositions

Examples 23-33 illustrate compositions falling outside the scope of the present invention which contain clobetasol propionate of formula (I).

Tables 1D-1E illustrates the quantitative composition of the comparative compositions of Examples 23-33, wherein the amount of the components is expressed in percentage (%) by weight of each ingredient in relation to the total weight of the composition.

In particular, the comparative compositions 24, 25, 26 and 29 fall outside the scope of the present invention because the weight ratio between the oil components and the sum of the oil components and surfactant is 0.7 being above the proposed limit of 0.5. Furthermore the percentages of oils and surfactants are higher than those corresponding to the nanoemulsions of the present invention. The comparative compositions 30 and 31 are nanoemulsions with weight ratios between the surfactant and the clobetasol or a pharmaceutical acceptable salt or ester thereof higher than 200:1. The comparative compositions 23 and 27 fall outside the scope of the present invention because are not nanoemulsions. The compositions 23 and 27 are micellar solutions without the positive activity of oily components, and the composition 23 as well contains a high percentage of alcohol as described in the prior art of clobetasol formulations. The composition 28 is a suspension, thus clobetasol propionate is not properly dissolved. The compositions 32 and 33 are the placebos for the pharmacological studies.

TABLE 1D

| | Example | | | | |
|---|---|---|---|---|---|
| | 23 | 24 | 25 | 26 | 27 |
| Clobetasol propionate | 0.522 | 0.050 | 0.036 | 0.029 | 0.050 |
| Polysorbate21 | — | 20.997 | 15.000 | 12.351 | — |
| D-α-tocopheryl polyethylene glycol succinate (TPGS) | — | — | — | — | 5.000 |
| Isopropyl myristate | — | 48.963 | 35.000 | 28.802 | — |
| Ethanol | 9.533 | — | — | — | — |
| Polyethylene glycol, polyvinyl acetate and polyvinylcaprolactame-based graft copolymer (PVAc-PVCap-PEG) | 4.510 | — | — | — | — |
| Gellam gum | — | — | — | — | 0.350 |
| Glycerin | — | — | — | — | 2.100 |
| Water | q.s.* 100% | q.s.* 100% | q.s.* 100% | q.s.* 100% | q.s.* 100% |

"q.s." means quantity sufficient

TABLE 1E

| Example | 28 | 29 | 30 | 31 | 32 | 33 |
|---|---|---|---|---|---|---|
| Clobetasol propionate | 0.100 | 0.052 | 0.050 | 0.050 | — | — |
| Polysorbate80 | — | — | 7.512 | — | 5.000 | 5.008 |
| Polysorbate21 | — | 12.756 | 29.988 | 40.022 | — | — |
| Cremophor ®RH40 | — | — | — | — | — | — |
| Mineral oil | — | — | 12.501 | — | — | — |
| Isopropyl myristate | — | 29.045 | — | — | — | — |
| Isopropyl palmitate- | — | — | — | 10.024 | — | — |
| Medium chain triglycerides | — | — | — | — | 0.504 | 0.522 |
| Petrolatum | q.s.* 100% | — | — | — | — | — |
| Benzalkonium chloride | — | — | — | — | 0.010 | 0.010 |
| EDTA | — | — | — | — | 0.100 | 0.100 |
| Povidone | — | — | — | — | 5.000 | 5.009 |
| Tris(hydroxymethyl)aminomethane hydrochloride | — | — | — | — | 0.839 | 0.661 |
| Tris(hydroxymethyl)aminomethane | — | — | — | — | 0.052 | 0.148 |
| Glycerin | — | — | — | — | 0.958 | 1.062 |
| Water | — | q.s.* 100% | q.s.* 100% | q.s.* 100% | q.s.* 100% | q.s.* 100% |

"q.s." means quantity sufficient

C. Comparative Buffered Solutions

Comparative buffered solutions illustrate compositions falling outside the scope of the present invention which contain clobetasol propionate of formula (I). These comparative buffered solutions are used in the stability test (cf. section 1.3.)

Table 2 illustrates the quantitative composition of the comparative buffered solutions at pH 6.0, pH 6.8 and pH 7.4, wherein the amount of the components is expressed in grams in relation to the final volume of the solution.

TABLE 2

| Comparative buffered solutions | | pH | | |
|---|---|---|---|---|
| Components | units | pH 6.0 | pH 6.8 | pH 7.4 |
| Clobetasol propionate | g | 0.05 | 0.05 | 0.05 |
| Sodium dihydrogen phosphate monohydrate | g | 1.30 | 0.98 | 0.53 |
| Disodium hydrogen phosphate dihydrate | g | 0.11 | 0.51 | 1.10 |
| Acetonitrile/water (volume ratio 1:1) | ml | q.s*100 | q.s*100 | q.s*100 |

"q.s." means quantity sufficient 1.2. Preparation Process

A. Compositions of the Invention

The compositions of Examples 1-22 of the present invention were prepared following the process as defined below:

Step 1 (oil phase): In a suitable reactor was blended clobetasol propionate, oils and surfactants in order to obtain a homogenous mixture.

Step 2 (aqueous phase): In a separate reactor the water was disposed.

Step 3: The aqueous phase was added stepwise to the oil phase with stirring until nanoemulsion was obtained. Temperature of aqueous and oil phase were kept constant around 25° C.

Step 4: Other excipients or carriers were added in the aqueous phase, oil phase or nanoemulsion depending on their solubility.

B. Comparative Compositions

The comparative composition of Example 23 of the present invention was prepared following the process as defined below:

Step 1. In a suitable reactor clobetasol and ethanol were stirred until complete dissolution.

Step 2. In a suitable container, PVAc-PVCap-PEG was dissolved in water.

Step 3. The clobetasol solution was added stepwise to the polymer solution with a continuous stirring until a homogenous composition was obtained.

The comparative compositions of Examples 24-26 and 29-33 of the present invention were prepared following the process herein described Step 1 (oil phase): In a suitable reactor was blended clobetasol propionate, oils and surfactants in order to obtain a homogenous phase.

Step 2 (aqueous phase): Excipients not included in the oil phase were dissolved in water.

Step 3: The aqueous phase was added stepwise to the oil phase with stirring until nanoemulsion was obtained.

The comparative composition of Example 27 of the present invention was prepared following the process herein described:

Step 1. In a suitable reactor clobetasol and D-α-Tocopherol polyethylene glycol 1000 succinate (TPGS) were stirred until a homogeneous mixture was obtained.

Step 2. In a suitable container, gellan gum was dissolved in water.

Step 3. The water solution was added stepwise to the surfactant and clobetasol mixture with a continuous stirring until a homogenous composition was obtained.

Step 4. Glycerin was added and the formulation was stirred until homogeneity.

The comparative composition of Example 28 of the present invention was prepared following the process herein described:

Step 1. In a suitable reactor clobetasol and petrolatum were stirred until a homogeneous mixture was obtained.

C. Comparative Buffered Solutions

The comparative buffered compositions were prepared following the process herein described:

The sodium dihydrogen phosphate monohydrate and disodium hydrogen phosphate dihydrate were dissolved in the acetonitrile/water (volume ratio 1:1) and immediately after the clobetasol propionate was dissolved in the resulting media.

1.3. Stability Test

The chemical stability of the clobetasol propionate in the nanoemulsion compositions were compared to buffered solutions at the same pHs to evaluate the protective effect of the nanoemulsion.

A. Samples

Test samples: The nanoemulsion composition of the invention of Example 11 was adjusted to a pH of 6.0, 6.8 and 7.4.

Comparative buffered solution samples disclosed in section 1.2.

B. Method

The samples mentioned in section A were analysed separately following the analytical method for organic impurities described in the USP <18334> monograph Clobetasol Propionate available in the website of the pharmacopeia http://www.pharmacopeia.cn/v29240/usp29nf24s0_m18334.html#usp29nf24s0_m18334 on June 2017).

The chromatographic system employed consisted of an Agilent 1290 high performance liquid chromatography with ultraviolet detection at 240 nm. A Kromasil $C_{18}$ (150×4.6 mm, 5 μm) column was used for separation of the impurities.

Samples were prepared by diluting approximately 1 g of the each composition with water/acetonitrile (1:1) volume:volume up to a final volume of 5 ml.

C. Conditions

The samples were maintained at 70° C. for 24 hours at pH of 6.0, 6.8 and 7.4 respectively. After that time the samples were analysed.

D. Results

Table 3 illustrates the percentage of the total amount of degradation products and any individual degradation product detected after maintaining the samples under the conditions mentioned in section B. In particular, the amount of any individual degradation product as well as the total amount of degradation products expressed in weight percent (%) is shown in the Table below.

TABLE 3

| Degradation products (%) | pH | Test sample: Nanoemulsion of Example 11 adjusted at different pHs | Comparative buffered solutions of section 1.1.C |
|---|---|---|---|
| Any individual degradation product | 6.0 | 0.29 | 1.0 |
| | 6.8 | 0.26 | 3.2 |
| | 7.4 | 0.34 | 15.8 |
| Total degradation products | 6.0 | 0.49 | 3.4 |
| | 6.8 | 0.47 | 6.8 |
| | 7.4 | 1.0 | 53.5 |

As it is shown in the results of Table 3, the clobetasol propionate present in the nanoemulsion of the present invention is much more stable at all tested pH than the clobetasol propionate carried in the comparative phosphate buffered solution.

In particular, at pH 6.0 there are 7 times more of degradation products in the comparative solution than in the nanoemulsion of the present invention. Besides, at pH 6.8 there are 14 times more of degradation products in the comparative solution and, at pH 7.4 there are 53 times more of degradation products than in the nanoemulsion of the present invention.

Therefore, the nanoemulsion compositions of the present invention improves the stability of clobetasol propionate if compared to solutions, furthermore the compositions of the invention also comply with the strict regulatory affairs requirements of the specification of the ICH Harmonised Tripartite Guideline Impurities in New Drug Products Q3B (R2).

1.4. In Vitro Drug Release Performance Test

The aim of the performance test for topical compositions is the measurement of the drug release from the dosage form. The vertical diffusion cell (VDC or Franz cell) system is a simple, reliable, and reproducible mean of measuring drug release from coloidal dosage forms.

Drug release can be described by mathematical models based on diffusion equations like the model published by Higuchi, which is often used. This model describes the release of a drug as a function of the square root of time (slope $\mu g/h^{1/2}$) when sink conditions are maintained. The slope can be considered as the release rate of active ingredient from the tested composition.

A. Samples

Test samples: The nanoemulsion compositions of the invention of Examples 7, 11 and 22. Comparative samples: The comparative compositions of Examples 26, 28 and 29.

B. Method

Diffusive communication between the delivery system and the reservoir takes place through an inert, highly permeable support membrane (polysulfane Tuffryn membrane 0.45 μm). The membrane keeps the product and the receptor medium separate and distinct. The membrane was chosen to offer the least possible diffusional resistance and not to be rate controlling.

C. Conditions

The release rate experiment was carried out at 32° C.±1° C. To achieve sink conditions, the receptor medium was a 5% TPGS aqueous solution. The test and comparative samples were placed over the membrane disposed in a 15-mm diameter orifice Franz cell. Sampling was performed during 4 h, and the volume withdrawn was replaced with fresh receptor medium. The amount of clobetasol propionate in the acceptor was determined for every release cell at every sampling time following the analytical method for organic impurities described in the Clobetasol Propionate USP monograph available in the website of the pharmacopeia http://www.pharmacopeia.cn/v29240/usp29nf24s0_m18334.html#usp29nf24s0_m18334 on June 2017).

The average cumulative amount released (μg) was calculated for the different formulations tested, and a linear function was established using the square root of time as independent variable. The slope was the main factor to evaluate the drug release rate from different compositions.

D. Results

The release of clobetasol propionate from the compositions of the present invention and also from the comparative compositions disclosed in the present invention showed a good adjustment to the linear mathematical diffusion model. It is demonstrated for the value of coefficient ($R^2$) that is close to 1 as depicted in Table 4 below.

Table 4 illustrate the slope value expressed in $\mu g/h^{1/2}$ and the coefficient $R^2$ value.

TABLE 4

| Example | Slope ($\mu g/h^{1/2}$) | coefficient $R^2$ |
|---|---|---|
| Example 7 | 38.3 | 0.9973 |
| Example 11 | 42.1 | 0.9945 |
| Comparative Example 28 | 0.7 | 0.9924 |
| Comparative Example 29 | 6.5 | 0.9977 |
| Example 22 | 29.1 | 0.9916 |
| Comparative Example 26 | 4.8 | 0.9973 |

However, only the compositions of the present invention show a fast delivery of the active ingredient, meanwhile the comparative compositions has an incomplete and low delivery of clobetasol from the composition. The high slope values confirm the fast delivery of clobetasol in the compositions of the invention (cf. Examples 7, 11 and 22) meanwhile the comparative compositions (Examples 26, 28 and 29) show a low slope value which is correlated with a low and incomplete delivery.

In particular, the active ingredient carried in the nanoemulsions of the invention is released to the receptor media in a higher amount and rate compared to the comparative samples. However, the efficacy of comparative compositions are compromised since the clobetasol have a limited access to the targeted biological tissues, meanwhile the nanoemulsions allow the right release of active ingredient. This behaviour is specially suitable for ophthalmic, nasal or buccal administrations where the limited residence time is a challenge and the active ingredient must be delivered in a faster and effective maner.

2. Pharmacological Efficacy Study

A. Tolerability

A.1. In Vitro Tolerability

A.1.1. Cornea Cells In Vitro Tolerability Study (STE Method)

Samples

Test samples: Nanoemulsions of Examples 2, 4, 8, 11, 14, 16, 19 and 20.

Comparative samples: Nanoemulsions of the comparative Examples 24, 25, 26, 30 and 31.

Material and Method

The STE test method (OECD TG 491) is an in vitro method that evaluates the eye hazard potential of a test chemical (substances and mixtures) based on its ability to induce cytotoxicity. The aim of this experiment is to characterise the cytotoxic effect of the clobetasol propionate in ophthalmic nanoemulsions.

SIRC (Statens Serum Institut Rabbit Cornea) cells were seeded in sterile 96-well microfilter plates and maintained in culture until confluence. The test formulations were diluted in physiological saline (PBS) at the determined concentration and the culture medium was replaced by the clobetasol nanoemulsions during 5 minutes. After that, cell viability was determined by MTT assay. Cell mortality was expressed as percentage and it was calculated for each test concentration with regard to the physiological saline control.

Results

The tested nanoemulsions of the invention showed no cytotoxicity at the tested concentrations and therefore they were classified as minimal irritant by the STE score indicating no eye damage potential. However, the incubation of the compositions of comparative Examples mentioned above showed cytotoxic effects.

Therefore, the nanoemulsions of the present invention do not present ocular hazard potential and must be considered well tolerated at ocular level meanwhile comparative compositions would be irritant and not suitable for ophthalmic administration route.

A.1.2. Inner Ear Cells In Vitro Tolerability Study

Samples

Test samples: Nanoemulsions of Examples 2, 4, 8, 11, 14, 16 and 20.

Comparative samples: Nanoemulsions of the comparative Examples 24, 30 and 31.

Material and Method

The HEI-OC1 (House Ear Institute-Organ of Corti-1) cell line is one of the most used auditory cell line available for research purposes. The HEI-OC1 cells express several characteristic molecular markers of the organ of *Corti* sensory cells (cf. Kalinec G M, et al., "A cochlear cell line as an in vitro system for drug ototoxicity screening". *Audiol. Neurootol.* 2003; vol. 8, pp. 177-89).

The objective of this assay is to test the ototoxic potential of clobetasol propionate nanoemulsions for otic administration.

HEI-OC1 cells were plated in sterile 96-well microliter plates and after 24 hours were treated with the clobetasol nanoemulsions diluted in physiological saline (PBS) at 5% and 0.05% during 5 minutes. After that, cell viability was determined by MTT assay. Cell mortality was expressed as percentage and it was calculated for each test concentration with regard to the physiological saline control.

Results

No cytotoxicity was observed for the tested nanoemulsions of the invention. However, the incubation of the comparative compositions showed hight cell mortality at the concentration of 5%.

Therefore, the nanoemulsions of the present invention present low otic irritant potential meanwhile comparative formulations are not adequate for otic administration.

A.2. In Vivo Ocular Tolerability Study

Samples

Test sample: Nanoemulsion of Example 11 of the present invention.

Comparative sample: Comparative composition of Example 27.

Control Samples: vehicle of Example 32.

Material and Method

The aim of this study is to assess the ocular irritation potential of different formulations of clobetasol propionate.

Male New Zealand rabbits were used for the test.

The protocol used was based on the TG405: OCDE Guideline for testing of chemicals: Acute Eye Irritation/Corrosion (2012).

Rabbits were distributed in different groups including a control group and a test group. The treatment involved the administration to both eyes of each animal 7 times a day with the control sample, test sample and comparative sample as defined above. Therefore, each sample was placed in the subconjunctival sac after gently pulling the lower lid away from the eyeball. After application, the lids were closed and gently held together in order to prevent loss of material. The conjunctiva, cornea, eyelids and iris were examined using a slit-lamp according to grading of ocular lesions from TG405: OCDE Guideline for testing of chemicals: Acute Eye Irritation/Corrosion (2012) each day before the dosing and 30 minutes after the last dosing. Control non treated animals were used as reference.

Results

No ocular abnormalities (opacity, redness or swelling) were observed in the cornea, eyelid, iris or conjunctiva on the animal eyes treated after administration of the nanoemulsion of the present invention. Therefore, the nanoemulsion of the present invention must be considered not irritant at ocular level. However, results obtained with comparative sample, as mentioned above, showed to be irritant and not suitable for ophthalmic administration.

B. Study of Effect on Intraocular Pressure (IOP)

Samples

Test samples: Nanoemulsion of Examples 7 and 10.

Control samples:

Positive control: dexamethasone 0.1%.

Negative control: 0.9% sodium chloride saline solution

Material and Method

The laboratory animals used were normotensive albino New Zealand rabbits. The rabbits were adapted to periods of light/dark (12/12 hours) needed to adjust and maintain stable the diurnal cycle of the intraocular pressure (IOP).

Rabbits were distributed in different groups: the positive control group (positive control sample), the negative control group (negative control sample) and two test groups (two test samples).

The treatment involved the injection of dexamethasone into the anterior chamber, meanwhile for the rest of groups; each animal was topically instilled, in each eye with the control sample or the test composition 4 times a day for 15 days.

Measurement of IOP of the groups was performed twice a day. After the instillation in each animal, it was observed the possibility of adverse effects of the respective compound on the ocular surface.

Results

The test of the nanoemulsions of the invention (Examples 7 and 10) showed no significant changes in intraocular pressure during the 15-day interval test. In particular, after the administration of the nanoemulsion of Example 7 no statistically significant elevation of the intraocular pressure was observed. Meanwhile, no changes were observed with the administration of the nanoemulsion of Example 10.

On the other hand, the animals treated with intra-cameral administration of dexamethasone (positive control group) presented statistically significant elevation of the intraocular pressure values.

Furthermore, no ocular surface adverse effects showing little changes or observations worthy of mention were observed in any of the ophthalmologic examinations for the tested samples.

Therefore, the nanoemulsions of the present invention should be considered safe during the treatment (that is during the instillation period of 15 days). Comparative samples were not suitable for testing in animal model because of the negative results obtained in the in vitro tolerability tests.

C. Anti-Inflammatory Efficacy Study

C.1. In Vitro Anti-Inflammatory Efficacy Study

Sample

Test samples: Nanoemulsion of Examples 2, 6, 7, 10, 11, 16, 21 and 22.

Material and Method

The THP-1 cell line is an immortal human monocytic cell line derived from an acute monocytic leukemia patient. THP-1 cells were plated, inflammation was induced with LPS and IFNγ and cells were incubated for 24 hours. After that, cells were treated with the test samples The formulations to be tested were diluted with culture medium and culture for other 24 hours. Protein concentration was measured by ELISA, using BDOptEIA Human TNFα Elisa Set according (BD 555212). The inhibition percentage of cytokine levels was calculated with regard to the stimulated group which was set to 100% expression levels.

Results

Nanoemulsion compositions of the invention showed anti-inflammatory activity reducing the protein expression of TNFα, with percentages of inhibition close to 100%. These results confirm the release of active ingredient to the culture medium and the right anti-inflammatory activity.

C.2. In Vivo Anti-Inflammatory Efficacy Study

C.2.1.i) Rabbit Model of Postsurgery Inflammatory (Paracentesis)

Samples

Test samples: Examples 10 and 18

Comparative sample: Example 23

Control samples:

Negative control 1: saline solution

Negative control 2: vehicle Example 33

Material and Method

The anti-inflammatory efficacy test is performed in a rabbit acute model of post-operative inflammation created by anterior chamber paracentesis.

Animals submitted to paracentesis were assigned to different groups: negative control group (negative control samples), comparative test group (comparative sample) and two test groups (test samples). Anterior chamber paracentesis was performed with a needle attached to a syringe and a sample of aqueous humour was removed. After 2 hours from the first paracentesis, a second paracentesis was performed to collect the aqueous humour for biochemical evaluation. Levels of Prostaglandin E2 (PGE2) in the aqueous humour were assessed by ELISA (R&D Systems SKGE004B).

Results

The aim of this study is to assess the anti-inflammatory efficacy of the clobetasol propionate of the nanoemulsion of the present invention.

Nanoemulsions of the present invention significantly reduced the aqueous humour concentration of $PGE_2$ compared with the control. However, the administration of the comparative composition did not show any effect on the $PGE_2$ biomarker, showing a clear lack of efficacy.

Therefore, the nanoemulsion of the present invention should be considered efficient for the treatment of ocular inflammatory disease or conditions.

3. Comparative Examples

The comparative compositions 34 and 35 disclosed below are the reproduction of the clobetasol propionate emulsions described in Mohammad Sajid Ali et al (cf. "mohammad Sajid Ali et al. "accelerated Stability Testing of a Clobetasol propionate Loaded nanoemulsion as per ICH guideline". Scientia Pharmaceutica, 2013, vol. 81, no.4, pp. 1089-1100).

3.1. Comparative Compositions

Table 5 illustrates the quantitative composition of the comparative compositions of Examples 34 and 35, wherein the amount of clobetasol propionate is expressed in mass concentration in relation to the total volume of composition (w/v); meanwhile the amount of the remaining ingredients of the composition is expressed in percentage (%) by volume in relation to the total volume of the composition (v/v).

TABLE 5

| | Comparative Example | |
|---|---|---|
| | Comp. Ex. 34 | Comp. Ex. 35 |
| Clobetasol propionate | 0.05% (w/v) | 0.05% (w/v) |
| Eucalyptus oil | 15% (v/v) | 15% (v/v) |
| Tween 20:ethyl alcohol (1:1) | 35% (v/v) | — |
| Tween 20:ethyl alcohol (1:2) | — | 35% (v/v) |
| Water | q.s.* 100.0% (v/v) | q.s.* 100.0% (v/v) |

"q.s." means quantity sufficient 3.2. Preparation Process 3.2.1. Comparative Example 34

The comparative clobetasol Example 34 having a ratio Smix 1:1 between tween 20 and ethyl alcohol was prepared following the process disclosed by Mohamed Sajid Ali in page 1092 section "preparation of clobetasol propionate nanoemulsion". This section is included herein below:

"[ . . . ] The optimized nanoemulsion was prepared by dissolving 0.05% (w/v) of clobetasol propionate (CP) in 15% (v/v) eucalyptus oil, then a 35% (v/v) mixture of Tween 20 and ethyl alcohol (1:1 v/v) were added slowly to the oil phase. Then the remaining amount of distilled water was added slowly to get the final preparation of 100% (v/v). A vortex mixer was used for the vigorous shaking of the mixture (oil, Smix, and water) [ . . . ]"

3.2.2. Comparative Example 35

The comparative clobetasol Example 35 having a ratio Smix 1:2 between tween 20 and ethyl alcohol (cf. page 1092 line 16) was prepared following the process disclosed by Mohamed Sajid in page 1092 section"preparation of clobetasol propionate nanoemulsion" disclosed above but changing the ratio of tween 20 and ethyl alcohol from 1:1 to 1:2.

3.3. Appearance and Measurement of the Droplet Average Size 3.3.1. Naked Eye Assessment After observation of the comparative examples 34 and 35 (just after their preparation) at naked eye, it was concluded that these compositions were opaque (non-transparent) liquid compositions having a low viscosity appearance.

3.3.2. Measurement of the droplet average size by Dynamic Light Scattering (DLS)

The average droplet size of the comparative Example 34 and 35 was analyzed by Dynamic Light Scattering (DLS). The equipment determined high polidispersion of the sample suggesting values of droplet average size above 6000 nm.

3.3.3. Conclusion

The lack of transparency of the comparative examples 34 and 35 is indicative that the droplet sizes of the comparative compositions 34 and 35 disclosed in Mohammad Sajid Ali et al are much higher than a nanoemulsion (translucent). Furthermore, as the droplet size measured by DLS showed high dispersion and droplet size values above 6000 nm, it means that the droplet size of the comparative compositions does not correspond to nanoemulsions droplet average size range (1-500 nm).

Therefore, from all disclosed above, it was understood that the droplet size of the comparative Examples 34 and 35 was higher than 6,000 nm (which is the high detection point of the DLS) being outside of the claimed range, and then they has to be considered emulsions instead of nanoemulsions.

3.4. Stability Test

The comparative compositions 34 and 35 were destabilized evolving into three differentiated phases instead of maintaining an homogenous and uniform appearance. The studies were performed at 25±2° C./60±5% relative humidity (RH), and changes were observed before 1 week of storage time.

Therefore, the comparative compostions 34 and 35 do not have colloidal stability.

3.5. Osmolality Test 3.5.1. Samples

Test sample: comparative compositions 34 and 35

3.5.2. Material and method

The osmolality is determined by the measurement of the freezing point depression of the sample using an osmometer.

3.5.3. Results

The osmolality of the comparative compositions 34 and 35 was higher than the claimed range of the present invention (i.e. 100 mOsm/Kg to 500 mOsm/Kg). Particularly, both comparative compositions had an osmolality higher than 2500 mOsm/Kg. It is specially remarkable that the comparative composition 34 has an osmolality of 2716 mOsm/Kg. (USP General Chapter <771>Ophthalmic Products, see osmolality and osmolarity <785>: ophthalmic products may be tolerated from 171 mOsm/kg to about 1711 mOsm/kg). The osmolality value of the comparative compositions was much higher than the tolerated osmolality for ophthalmic application, which is from 171 mOsm/kg to 1711 mOsm/kg.

Therefore, the comparative composition 34 and 35 were not appropriate for ophtalmic application. The nasal and otic compositions as well require isotonic or slightly hipertonic or slightly hipotonic compositions due to the sensitivity of nasal and otic tissues. Accordingly compositions 34 and 35 were not suitable for nasal or otic delivery routes of administration.

3.6. Cornea Cells In Vitro Tolerability Study (STE Method)

3.6.1. Samples, Material and Method

This assay was performed as disclosed in section A.1.1. above but using the comparative compositions 34 and 35 as test samples.

3.6.2. Results

The tested comparative compositions 34 and 35 showed cytotoxicity at the tested concentrations and therefore they were classified as toxic by the STE score.

Therefore, the comparative compositions 34 and 35 were not adequate for ophtalmic administration.

3.7. Inner Ear Cells In Vitro Tolerability Study 3.7.1. Samples, Material and Method This assay was performed as disclosed in section A.1.2. above but using the comparative compositions 34 and 35 as test samples.

3.7.2. Results

Cytotoxicity was observed for the tested comparative compositions 34 and 35. In particular, the incubation of the comparative compositions 34 and 35 showed hight cell mortality at tested concentration of 5%.

Therefore, the comparative compositions 34 and 35 were not adequate for otic administration.

3.8. Ocular Irritation Assay (HET-CAM)

3.8.1. Material and Method

The HET-CAM is a method which mimics vascular changes in the chorioallantoic membrane, an analogue for ocular conjunctiva, which can be used to determine the potential irritancy of a test substance. This method is based on that described in ICCVAM-Recommended Test Method Protocol: Hen's Egg Test—Chorioallantoic Membrane (HET-CAM) Test Method. NIH Publication No. 10-7533—Published 2010.

Fertilized white SPF (special pathogen free) White Leghorn chicken eggs were incubated at 37° C. and 60% humidity up to day 10. After determination of the viability of the embryo, a rectangular window was removed from the shell directly over the air cell and the egg membrane was carefully moistened with 2-3 ml 0.9% saline. After returning to the incubator for 30 minutes, the inner membrane was removed and the test substance was applied to the CAM membrane with a pipette. Eggs were observed continuously for 5 minutes for the appearance of lysis, haemorrhage and/or coagulation and an irritation score (IS) was determined following the ICCVAM-Recommended Test Method Protocol (NIH Publication No. 10-7553-Published 2010) guideline.

The irritation score (IS) is as follows:
Non-irritant: $0 \geq IS \geq 0.9$
slight irritant: $1 \geq IS \geq 4.9$
moderate irritant: $5 \geq IS \geq 9.9$
severe irritant: $10 \geq IS \geq 21$ 3.8.2. Results HET-CAM ocular irritation assay disclosed above was performed and the corresponding representative images of the tested samples were done (cf. FIG. 1).

In particular, the representative images reflected that the nanoemulsions of the present invention did not trigger any lysis, haemorrhage or coagulation processes, meanwhile the representative images reflected that the comparative composition 34 were irritant.

Furthermore, the irritation score (IS) of the composition of Ex. 7 and 11 and the comparative composition 34 were also determined. The values of the IS are disclosed in the Table below:

| Example Number | IS | |
| --- | --- | --- |
| Examples 7 and 11 | 0.07 | Non irritant |
| Comparative composition 34 | 14.46 | Severe irritant |

Thus, from the results mentioned above, it was understood that the compositions of the invention are non-irritant meanwhile the comparative compositions disclosed in Mohammad Sajid Ali et al were considered irritant and therefore, not suitable for being use as a medicament according to the proposed use of this invention.

3.9. Conclusion

The compositions disclosed in Mohammad Sajid Ali et al. were non-transparent emulsions having a droplet average size higher than 6,000 nm and an osmolality higher than 2500 mOsm/kg. Furthermore, the ratio oil/clobetasol is 272 and the ratio surfactant/clobetasol is 385, both higher than the claimed range in the compositions of the present invention.

Besides, the compositions disclosed in Mohammad Sajid Ali et al. did not have colloidal stability and also these compositions are irritant and therefore, not suitable for being used as a medicament.

CITATION LIST 1. 491 OECD Guideline for the testing of chemicals. Short Time Exposure in vitro test method for identifying i) Chemical inducing serious eye damage and ii) Chemicals not requiring classification for eye irritation or serious eye damage (2015). Available in the website http://www.oecd-ilibrary.org/docserver/download/9715201e.pdf?expires=1515680383&id=id&accname=guest&checksum=623490053F1D25E26DB7B437B0669A4B on july 2015.
2. Hassan, P. et al, "Making sense of Brownian motion: colloid characterization by dynamic light scattering", Langmuir, 2015, vol. 31, pp. 3-12.
3. ICH Harmonised Tripartite Guideline Impurities in New Drug Products Q3B(R2). Available in the website http://www.ich.org/products/guidelines/quality/quality-single/article/impurities-in-new-drug-products.html on june 2017.
4. Kalinec G M, Webster P, Lim D J, Kalinec F: A cochlear cell line as an in vitro system for drug ototoxicity screening. *Audiol. Neurootol.* 2003; 8:177-89.
5. TG405: OCDE Guideline for testing of chemicals: Acute Eye Irritation/Corrosion (2012). Available in the website http://www.oecd-ilibrary.org/docserver/download/9712201e.pdf?expires=1515680005&id=id&accname=guest&checksum=E0DCF0095196C8D17EBEBE86CA-F3D3DA on october 2012.
6. USP <18334> monograph Clobetasol Propionate. Available in the website http://www.pharmacopeia.cn/v29240/usp29nf24s0_m18334.html#usp29nf24s0_m18334 on june 2017.
7. The European patent number EP0844001.
8. The PCT patent application WO2017037663.

9. ICCVAM-Recommended Test Method Protocol: Hen's Egg Test—Chorioallantoic Membrane (HET-CAM) Test Method (NIH Publication No. 10-7553-Published 2010) guideline. Available in the website https://ntp.niehs.nih.gov/iccvam/docs/protocols/ivocular-hetcam.pdf on december 2017.

10. Mohammad Sajid Ali et al. "Accelerated Stability Testing of a Clobetasol propionate Loaded nanoemulsion as per ICH guideline". Scientia Pharmaceutica, 2013, vol. 81, no. 4, pp. 1089-1100).

The information claimed is:

1. An oil-in-water nanoemulsion composition having a continuous aqueous phase and dispersed oil droplets, wherein the nanoemulsion comprises:
   (a) a therapeutically effective amount of clobetasol or a pharmaceutically acceptable salt or ester thereof;
   (b) one or more oil components; and
   (c) one or more surfactants;
   together with one or more pharmaceutically acceptable excipients or carriers wherein:
   the osmolality of the nanoemulsion composition is comprised from 100 mOsm/Kg to 500 mOsm/Kg;
   the droplet average size is comprised from 1 nm to 500 nm measured by Dynamic light scattering;
   the weight ratio between the oil components and the sum of the oil components and one or more surfactants is comprised from 0.001 to 0.5;
   the weight ratio between the oil component and clobetasol or a pharmaceutically acceptable salt or ester thereof is comprised from 1:1 to 200:1; and
   the weight ratio between the surfactant and clobetasol or a pharmaceutically acceptable salt or ester thereof is comprised from 2:1 to 200:1.

2. The oil-in-water nanoemulsion composition according to claim 1, which comprises from 0.001% to 0.1% by weight of clobetasol propionate.

3. The oil-in-water nanoemulsion composition according to claim 1, wherein the pH is comprised from 4.0 to 8.0.

4. The oil-in-water nanoemulsion composition according to claim 1, wherein the weight ratio between the oil components and the sum of the oil components and one or more surfactants is comprised from 0.001 to 0.4.

5. The oil-in-water nanoemulsion composition according to claim 1, wherein the weight ratio between the oil component and clobetasol or a pharmaceutically acceptable salt or ester thereof is comprised from 1:1 to 100:1.

6. The oil-in-water nanoemulsion composition according to claim 1, wherein the weight ratio between the surfactant and clobetasol or a pharmaceutically acceptable salt or ester thereof is comprised from 2:1 to 190:1.

7. The oil-in-water nanoemulsion composition according to claim 1, wherein the amount of ethanol in the nanoemulsion composition is comprised from 0% to 3% by weight.

8. The oil-in-water nanoemulsion composition according to claim 1, wherein the oil component is selected from the group consisting of castor oil; glyceryl monostearate; ethyl oleate; decyl oleate; isopropyl miristate; isopropyl palmitate; isopropyl isostearate; isostearyl isostearate; myristyl lactate; mineral oil; light mineral oil; vegetable oils; monoester, diester or triester of glycerin and ($C_6$-$C_{12}$) alkyl fatty; and mixtures thereof.

9. The oil-in-water nanoemulsion composition according to claim 1, wherein the surfactant is a non-ionic surfactant selected from the group consisting of sorbitan esters ethoxylates derivatives, sorbitan esters derivatives, poly(ethylene oxide)-poly(propylene oxide) copolymers, polyoxyl 35 castor oil, polyoxyl 40 hydrogenated castor oil, polyoxyl 40 stearate, octoxynol 40, D-α-Tocopherol polyethylene glycol 1000 succinate (TPGS), and mixtures thereof.

10. The oil-in-water nanoemulsion composition according to claim 1, further comprising a pH adjusting agent selected from the group consisting of acetic acid, boric acid, sorbic acid, citric acid, sodium phosphate, dibasic sodium phosphate, monobasic sodium phosphate, potassium dihydrogen phosphate, hydrochloric acid, sodium hydroxide, sodium thiosulfate, sodium sulfite, sodium sulphate, tris(hydroxymethyl)aminomethane, tris(hydroxymethyl)aminomethane hydrochloride, sodium hydrogen carbonate, sodium borate, sodium acetate, sodium bisulphate, sodium benzoate, sodium citrate and mixtures thereof.

11. The oil-in-water nanoemulsion composition according to claim 1, further comprising a tonicity agent selected from the group consisting of sodium chloride, glycerin, glucose, mannitol, sorbitol, propylene glycol and mixture thereof.

12. The oil-in-water nanoemulsion composition according to claim 1, which is in form of an ophthalmic composition, a nasal composition, otic composition or buccal composition.

13. A process for the preparation of the oil-in-water nanoemulsion composition as defined in claim 1, which comprises:
   (a) preparing the oil phase by mixing clobetasol with the oil components and the surfactants;
   (b) preparing the aqueous phase;
   (c) emulsifying the oil phase obtained in step (a) in the aqueous phase obtained in step (b);
   (d) optionally, adjusting the pH; the osmolality; the pH and the osmolality after step (a), step (b) or step (c); and
   (e) optionally, adding one or more additional pharmaceutically acceptable excipients or carriers in step (a), step (b) or step (c).

14. A method for the prophylaxis and/or treatment of an inflammatory disease or condition in a mammal suffering from or susceptible to suffer from an inflammatory disease or condition, wherein the method comprises administering to said mammal the nanoemulsion composition as defined in claim 1 which comprises a therapeutically effective amount of clobetasol or a pharmaceutically acceptable salt or ester thereof together with one or more pharmaceutically acceptable excipients or carriers.

* * * * *